(12) United States Patent
Hasegawa et al.

(10) Patent No.: US 10,365,222 B2
(45) Date of Patent: Jul. 30, 2019

(54) BIOCHIP FOR RAMAN QUANTITATIVE ANALYSIS OF BIOLOGICAL SAMPLES

(71) Applicant: MYTECH CO., LTD., Hyogo (JP)

(72) Inventors: Yuki Hasegawa, Hyogo (JP); Katsuyuki Hasegawa, Hyogo (JP)

(73) Assignee: MYTECH CO., LTD., Hyogo (JP)

( * ) Notice: Subject to any disclaimer, the term of this patent is extended or adjusted under 35 U.S.C. 154(b) by 70 days.

(21) Appl. No.: 15/314,996

(22) PCT Filed: May 8, 2014

(86) PCT No.: PCT/JP2014/062315
§ 371 (c)(1),
(2) Date: Nov. 30, 2016

(87) PCT Pub. No.: WO2014/181814
PCT Pub. Date: Nov. 13, 2014

(65) Prior Publication Data
US 2017/0248523 A1  Aug. 31, 2017

(30) Foreign Application Priority Data

May 8, 2013 (JP) .................. 2013-098608

(51) Int. Cl.
*G01N 21/65* (2006.01)
*C01G 5/00* (2006.01)
(Continued)

(52) U.S. Cl.
CPC ............ *G01N 21/658* (2013.01); *C01G 5/00* (2013.01); *G01N 33/5438* (2013.01);
(Continued)

(58) Field of Classification Search
CPC ............ G01N 21/658; G01N 33/5438; G01N 33/553; G01N 33/57496; C01G 5/00
(Continued)

(56) References Cited

U.S. PATENT DOCUMENTS 4,478,943 A * 10/1984 Abe ................ G01N 31/22
436/80
9,139,907 B2 9/2015 Hasegawa et al.
(Continued)

FOREIGN PATENT DOCUMENTS

JP  2007525662 A  9/2007
JP   200914491 A  1/2009
(Continued)

OTHER PUBLICATIONS

Yang, Z. et al. (2014). Particle-Arrayed Silver Mesocubes Synthesized via Reducing Silver Oxide Mesocrystals for Surface-Enhanced Raman Spectroscopy. Particle & Particle Sys Char. 31:390-397.*
(Continued)

*Primary Examiner* — Jill A Warden
*Assistant Examiner* — Jacqueline Brazin
(74) *Attorney, Agent, or Firm* — Raju Dave; Dave Law Group, LLC

(57) ABSTRACT

Object: To provide a biochip for use in exhaustive analysis of a particular protein including DNA (deoxyribose nucleic acid) in a body fluid through Raman quantitative analysis. Resolving Means: Aqueous solution of metal complexes including plasmon metal selected from the group consisting of Au, Ag, Pt and Pd is supplied dropwise onto a carrier metal having an electrode potential of metal less noble than complex metal, followed by precipitation of nanometric quantum crystals from the metal complex on the carrier metal, the metal complex being so selected as to have a complex stability constant (log β) that is expressed by the following equation (I) correlating with the electrode potential E of the carrier metal:

$$E° = (RT/|Z|·F)\ln(\beta_i) \qquad (I)$$

(Continued)

Qautum crystal shows a thin hexagonal column shapes
Non-clear facet of metal nano-crystal could not be observed Silver particles made by a conventional method
TEM images of silver nano-particles made by citric acid reduction of silver nitrate Appearance of facets shows metal silver nano crystals The above nano-structure seems to be different from that of silver Particles made by the conventional method (wherein E° represents the standard electrode potential, R represents a gas constant, T represents the absolute temperature, Z represents the ion valency, and F represents the Faraday constant), the surface property of the metal complex quantum crystals on the carrier metal being subsequently adjusted in dependence on an object to be detected in the aqueous solution prior to the precipitation or after the precipitation.

10 Claims, 19 Drawing Sheets

(51) Int. Cl.
    *G01N 33/553*     (2006.01)
    *G01N 33/543*     (2006.01)
    *G01N 33/574*     (2006.01)

(52) U.S. Cl.
    CPC ..... *G01N 33/553* (2013.01); *G01N 33/57496* (2013.01); *C01P 2002/60* (2013.01)

(58) Field of Classification Search
    USPC ..................................................... 422/82.05
    See application file for complete search history.

(56) References Cited

U.S. PATENT DOCUMENTS

| | | |
|---|---|---|
| 2005/0148098 A1 | 7/2005 | Su et al. |
| 2010/0186999 A1* | 7/2010 | Kuramoto ............... H01L 33/62 |
| | | 174/257 |
| 2011/0165586 A1 | 7/2011 | Kim et al. |
| 2012/0115245 A1* | 5/2012 | Hasegawa .............. B82Y 15/00 |
| | | 436/501 |
| 2013/0230660 A1* | 9/2013 | Hase .................... G01N 21/658 |
| | | 427/457 |

FOREIGN PATENT DOCUMENTS

| | | |
|---|---|---|
| JP | 201181001 A | 4/2011 |
| WO | 2010101209 A1 | 9/2010 |
| WO | 2012033097 A1 | 3/2012 |
| WO | 2013065747 A1 | 5/2013 |

OTHER PUBLICATIONS

International Search Report dated Aug. 12, 2014 in International Application PCT/JP2014/062315.

* cited by examiner

Fig.1 Method of calculating peaks of Raman wave
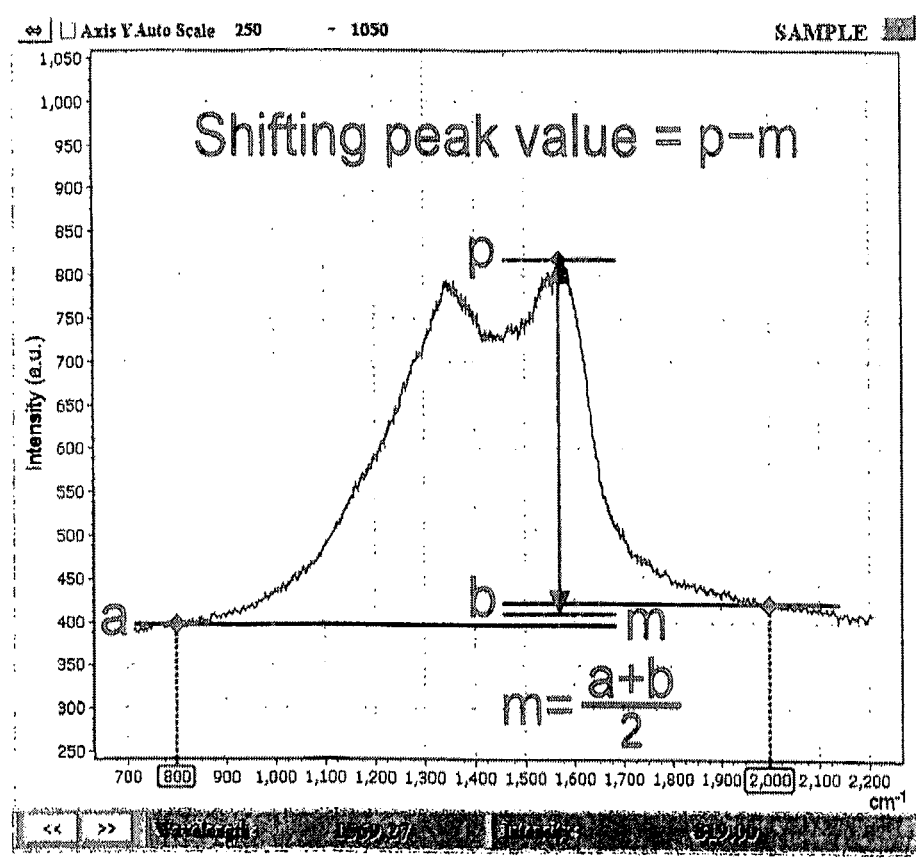

The diluted samples and the intensity of Raman scattering spectra

Fig.8
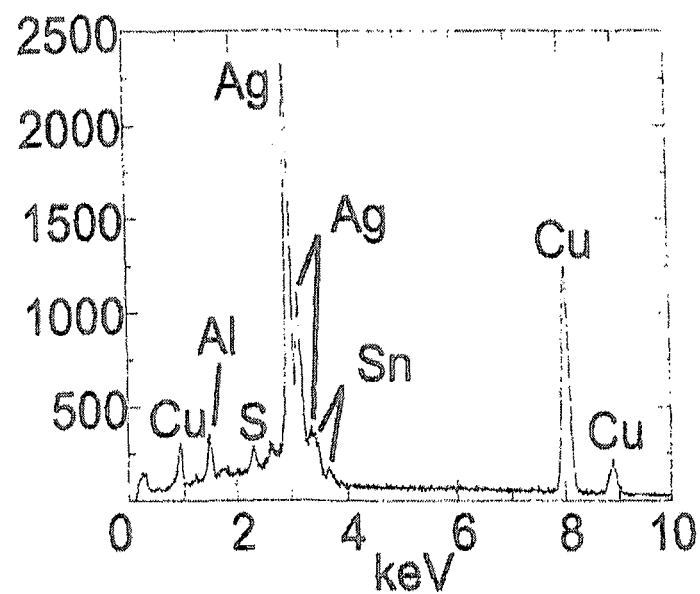
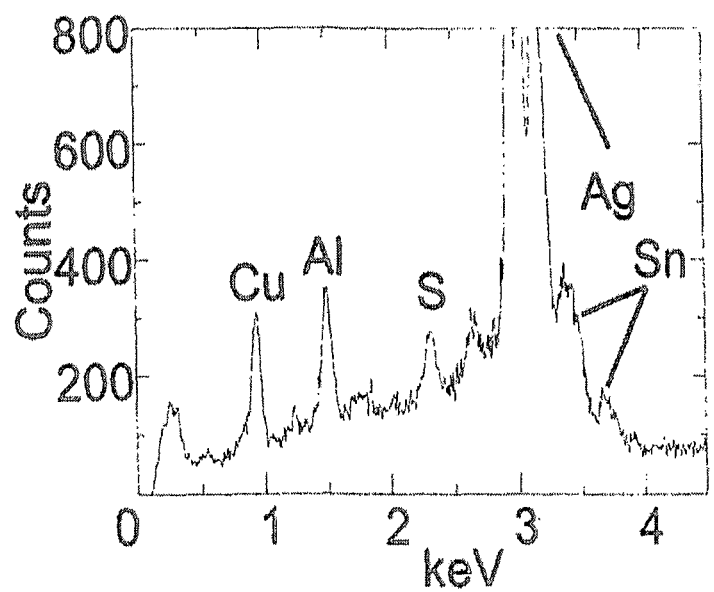

(a) Methylation  (b) Acetylation

BIOCHIP FOR RAMAN QUANTITATIVE ANALYSIS OF BIOLOGICAL SAMPLES

CROSS REFERENCE TO RELATED APPLICATION

This application is a national stage application, filed under 35 U.S.C. § 371, of PCT Application No. PCT/JP2014/062315, filed on May 8, 2014, entitled "BIOCHIP FOR RAMAN QUANTITATIVE ANALYSIS OF BIOLOGICAL SAMPLES", which claimed priority to Japanese Application No. 2013-098608, filed on May 8, 2013, all of which are hereby incorporated by reference in their entirety.

TECHNICAL FIELD

The present invention relates to a biochip for use in Raman quantitative analysis of a biological sample.

BACKGROUND ART

In order to acquire information useful in diagnosis, stage classification understanding and treatment of human diseases, it is necessary to know the sequences of human protein that are estimated in excess of 30,000 and to identify the important change in expression of protein that announces imminent crisis of the disease. It is also necessary to accurately classify the subtype of the disease on the molecular level so that the function, interrelation and activity of the protein closely related with the process of the disease can be adjusted. One of the bottommost ways to understand the function of the protein is to functionally associate the change of the level of expression with the vegetative stage, cell cycle state, stage of the disease, external stimulation, expression level or any other variable and, although DNA microarray analysis leads to mRNA expression assay method on the genome scale, no direct relation is often found between the in-vivo concentration of mRNA and the coded protein. Accordingly, the difference in speed of translation of mRNA to protein and the difference in speed of in-vivo proteolysis are considered a factor that results in disturbance to the extrapolation of mRNA to the protein expression profile.

Also, such a microarray assay referred to above often plays an important role in protein functional regulation, but is unable to detect, identify or quantitatively determine the protein modification.

Accordingly, the quantitative analysis against the detection and the analysis of analyte of a low concentration contained various biological samples generally necessitates labelling with the use of a radioactive isotope or a fluorescence reagent, and such method generally requires a substantial amount of time and is, hence, inconvenient to accomplish. For example, although various qualitative analyzing methods, two dimensional electrophoretic method and liquid chromatography have been widely used for the protein profiling, they are not adequate for use in summary survey.

Yet, in view of the solid state sensor, particularly biosensor, that is increasingly used in chemical, biological or pharmaceutical studies, such sensor is in recent years drawing unprecedented attention and makes use of a conversion structure capable of converting two elements; a recognition element of high uniqueness and a molecular recognition event, into a quantifiable signal and has been developed with the aim of detecting various biological molecular complexes including oligonucleotide pairs, antibody-antigen complex, hormone-acceptor complex, enzyme-substrate complex and lectin-glycoprotein complex interaction, but it still insufficient.

In view of the foregoing, the use of Raman scattering spectroscopy or a surface plasmon resonance has been suggested with the aim of accomplishing an objective to enable a highly accurate detection or identification of individual molecules in the biological sample. The wavelength of Raman scattering spectroscopy is characteristic of a chemical composition and structure of Raman scattering molecules in the sample and the intensity of Raman scattered light depends on the molecular concentration in the sample. In the practice of Raman scattering spectroscopy, nanoparticles of gold, silver, copper and any other plasmon metal exhibit a surface intensified Raman scattered effect in response to the applied laser beams and, using it, biological molecules of interest are characterized such that nucleotide, deoxyadenosine monophosphate, protein and hemoglobin could be detected at a single molecular level. As a result, however, SERS (surface enhanced Raman spectroscopy) could not be considered suitable for use in quantitative analysis of the protein content in the complex biological sample such as blood plasma.

In view of the foregoing, the need has arisen of a method of analyzing the protein composition of a sample of the complex organism in blood serum or the like with the use of Raman scattering spectroscopy to detect or identify the individual proteins with reliability, as well as high throughput means for quantitatively and qualitatively detecting the protein of a low concentration level in a composite sample. Accordingly, a method for analyzing the protein content in a biological sample has been suggested, in the patent document 1 listed below, which method includes isolating protein and protein segments in the sample based on chemical and/or physical characteristics of the protein, maintaining in an isolated condition the isolated proteins at the discrete positions on a solid substrate or in the flow of liquid then flowing, detecting Raman spectrum formed by the isolated proteins at the discrete positions so that through the spectrum at the discrete positions, information on the structure of one or more particular proteins at discrete positions can be provided. Also, SERS phenomenon involves some problems to be resolved in terms of repeatability and reliability because of (1) the mechanism not yet comprehended impeccably, (2) difficulties in formation of the nano-material, which is accurately and structurally defined, and in control, and (3) change in enhancement efficiency brought about by wavelength of light used in measurement of the spectrum and direction of polarization and, therefore, application of SERS including development and commercialization of the nano-biosensor is considerably affected. For this reason, a technique has been suggested, in the patent document 2 listed below, in which a hybrid structure of nanowire and nanoparticles is utilized to enhance SERS signals of such biomolecular as bio-extract and protein, DNA, repeatability of measurement and increase of sensitivity and reliability.

THE PRIOR ART

Patent Document 1: JP Laid-open Patent Publication No. 2007-525662
Patent Document 1: JP Laid-open Patent Publication No. 2011-81001

It has, however, been found that the first mentioned conventional method has a problem in that it is difficult to isolate the protein and the protein segments in the sample and is therefore difficult to fix on the substrate, whereas in the last mentioned conventional method, no efficient utilization is made in quantitative determination of the protein in the sample. The present invention has been developed to substantially eliminate the above discussed problems and inconveniences and is intended to provide a biochip for use in SERS analysis, in which the protein in each of the samples can be easily adsorbed on the chip and in which quantitative determination of the specific protein, including DNA related substances, can be accomplished easily through laser irradiation and, also, to provide a method capable of identifying a particular disease from the profile of particular proteins including DNA related substances and analyzing the degree of progress. In the course of the present invention, the inventors of the present invention have found, as a result of studies committed with all their heats, that, where a metal complex is to be formed in an aqueous solution, the metal complex having a high complex stability constant, for example, a high complex stability constant defined by polydentate ligands, for example, two or more bidentate ligands, when it is deposited out by means of the reductive reaction taking place in the vicinity of equilibrium potential, the metal complex is deposited out on the metal substrate as a quantum crystal. The inventors of the present invention have also found that the metal complex exhibits such a physical property as to adsorb the proteins contained in a biological sample, enough to facilitate formation of a solid phased surface suitable for use in various detections. The inventors of the present invention have furthermore found that where metal of the metal complex is a plasmon metal, possibly because quantum dots in the order of nanometer (say, 5 to 20 nm) are regularly distributed to form quantum crystals (100 to 200 nm) of the internally capsulated metal complex, nanometric metal clusters so properly distributed exhibits a surface plasmon resonance enhancing effect as a metal against Raman light and, along therewith, the quantum crystals adsorb analyte to form electrical charge transfer complexes to thereby form the biochip suitable for use in SPR or SERS analysis.

The present invention has been found and then completed as a consequence that, when based on those findings as discussed above, a blood plasma is dropwise supplied onto the metal complex quantum crystal, the particular protein mass, including DNA related substances in the blood plasma, can be quantified and, yet, a significant difference is found in the particular protein masses, including DNA related substances, between normally healthy subjects and cancer affected patients and, therefore, identification of types of cancer and the degree of process of the cancer can be determined by means of the exhaustive analysis on Raman spectrum so obtained. If so required, the polarity or surface property of the quantum crystal may be adjusted, a biological sample selected from the group consisting of urea, blood, blood plasma, blood serum, saliva, seminal fluid, human waste, cerebral fluid, tear, mucin, exhaled component and so on is supplied dropwise, Raman spectrum is obtained by irradiating the protein in the biological sample, fixed on the quantum crystal, with laser light of a particular wavelength, and a biochip capable of achieving a disease analysis from the particular protein analysis including DNA related substances in the biological fluid, through analysis of the disease from exhaustive information such as, for example, the peak height of Raman spectrum so obtained, the peak integrated value, the peak representation time and so on. Accordingly, in the practice of the present invention, an aqueous solution of metal complex including a complex of plasmon metal selected from the group consisting of Au, Ag, Pt and Pd is dropwise applied onto a carrier metal having an electrode potential, which is less noble than complex metal, to thereby allow the metal complex to be precipitated on the carrier metal in the form of quantum crystal of nanometric size. The metal complex is so selected as to have a complex stability constant (log β) equal to or less noble (higher) than that expressed by the following formula which correlates with the electrode potential E of the carrier metal:

$$E°(RT/|Z|\cdot F)\ln(\beta_i)$$

(In this formula (1) above, E° represents the standard electrode potential, R represents a gas constant, T represents the absolute temperature, Z represents the ion valency, and F represents Faraday constant.)

The biochip of the present invention is preferably such that the surface property or the electric potential of the metal complex quantum crystals on the carrier metal is adjusted in dependence on an object to be detected in the aqueous solution prior to the precipitation or after the precipitation. The biochip of the present invention is preferably such that the metal complex quantum crystal in the carrier metal adjusts the surface property or the electric potential within the aqueous solution prior to precipitation or in accordance with an object to be detected subsequent to precipitation. In utilizing the antigen-antibody reaction, when the antigen or the antibody is mixed in the aqueous solution of metal complex to precipitate the quantum crystal, the quantum crystal can be dispersed in a manner similar to the ligand. It appears that the antigen or the antibody mixed in the aqueous solution of metal complex is precipitated in mixed form during the precipitation of the metal complex in a manner similar to the ligand of the metal complex. Accordingly, it can be used in detection using protein binding with blood plasma, detection using protein binding with calcium, and detection using protein binding with sugar (lectin) (infection disease and immunologic disease).

It has been found that when the alkaline treatment is carried out with the use of an aqueous solution of sodium hypochlorite used for an alkaline aqueous solution containing halogen ions after the precipitation of the quantum crystal of the metal complex, silver oxides including silver peroxide are aggregated as a result of self-assembly under the apparent influence of the electrode potential of the substrate in the case of silver thiosulfate quantum crystal and therefore meso-crystal, which is of a super structure in which they are arrayed in three dimension in neuron form when recrystallized In the case of the metal complex being a silver complex, it has been found that the silver complex is formed as a result of the reaction between a silver complexing agent, having a stability constant (formation constant) (log $\beta_i$) which is 8 or higher, and silver halide. When the complexing agent is selected from the group consisting of thiosulfate, thiocyanate, sulfite salt, thiourea, potassium iodide, thiosalicylic acid salt and thiocyanuric acid salt, only a silver ion is not reduced, but the silver complex itself is precipitated as quantum crystals of the silver complex.

The complex has quantum dots of a nanometric size having an average particle size within the range of 5 to 20 nanometer and the size of the quantum crystals is within the range of 100 to 200 nm. The silver concentration of the metal complex in the aqueous solution is preferably within the range of 500 to 2,000 ppm.

As discussed above, it has been found that silver oxide containing silver peroxide, which is obtained by applying the alkali treatment (sodium hypochlorite) in the presence of halogen ions where the quantum crystal is silver thiosulfate, and the silver oxide meso-crystal, which is a super structure which is arrayed in three dimension in neuron form exhibit not only its structural characteristic, but also a negative charge in water, and adsorb cancer associated substances, which are positive charges, to form charge transfer complex and, also, the silver oxide meso-crystals are capable of changing into silver particles when irradiated with an exciting light, so that the surface plasmon enhancing effect can be obtained on the silver particles when irradiated with an exciting light such as laser. Accordingly, according to the present invention, the biochip provided with silver oxide meso-crystal can be used for Raman quantitative determination of the cancer associated substance.

With the biochip designed in accordance with the present invention, because of easiness of being charged with positive charge due to the characteristic of the metal complex, it is suited for use in adsorbing material propense to be charged with the negative charge in the aqueous solution. When an appropriate ligand is mixed in the aqueous solution of the metal complex at the time the metal complex is precipitated, the ligand can be mixed into the quantum crystal. By way of example, endotoxic can be detected if a limulus reagent (LAL reagent) mixed with the aqueous solution of metal complex of the present invention is precipitated onto the substrate as the quantum crystal. Also, in the utilization of properties of the quantum crystal precipitated on the substrate, a detecting regent for antibody or the like can be solid phased. On the other hand, in the biochip of the present invention, when the quantum crystal of the metal complex is treated with alkali in the presence of halogen ion, the quantum crystal can be recrystallized as a metal oxide crystal. Since when the quantum crystal of silver thiosulfate is treated with alkali in the presence of chlorine ion, mesocrystal of silver oxide including silver peroxide (AgO or $Ag_2O_3$) is formed, it is susceptible to be charged with negative charge in the aqueous solution and, hence, quantification of the particular protein as well as DNA related substances in the biological fluid are realized to allow various diseases to be predictable and the degree of progress thereof can be affirmed. As a result of the presence of the significant difference in amount of protein in the blood plasma between the normal person and the cancer affected patient, identification of the type of cancer and the degree of progress thereof can be determined and, therefore, immediate diagnosis of the cancer, determination of the cancer treatment policy, determination of curative medicine and curative effect, determination of the metastasis of cancer, and determination of recurrence of cancer can become easily determined by means of this blood examination. Accordingly, if the biochip of the present invention is properly used and the use is made of other biological samples urea, blood, blood plasma, blood serum, saliva, seminal fluid, human waste, phlegm, cerebral fluid, tear, mucin, exhaled component and so on are used, the protein profile unique to the particular diseases is detected to give out information on the early discovery of the disease and the degree of progress of the disease through a simple examination.

The term "biological sample" referred to above and hereinafter is to be understood as meaning a sample including a sample containing an analyte containing hundreds of proteins such as biological fluid of a host. The sample may be provided for use directly in Raman analysis or may be pretreated so as to modify protein containing molecules in the sample or segmentalize, whichever the sample is prepared for each detection. Also, the analyte, which is a target to be measured, may be determined by detecting material capable of evidencing a target analyte such as, for example, particular binding pair members complemental to the analyte of the target to be measured which exists only when the analyte forming the target to be measured exists in the sample, but the disease is preferably identified by means of Raman spectrum analysis for exhaustively detecting the particular protein including DNA related substances. Accordingly, the material evidencing the analyte becomes an analyte that is detected during the assay. The biological sample may be, for example, urea, blood, blood plasma, blood serum, saliva, seminal fluid, human waste, phlegm, cerebral fluid, tear, mucin, or a exhaled component.

The term "protein" referred to above and hereinafter is to be understood as including peptide, polypeptide and a protein containing analyte such as protein, antigen, sugar protein, riboprotein and others.

In one embodiment of the present invention, a method is provided for securing information on protein composition from a composite biological sample such as, for example, a patient sample. The protein in the sample may be arbitrarily modified with the use of a medical agent selected from the group consisting of a reducing agent, a surfactant, chaotropic salt and others. Although general chemical substances that can be used to reduce the disulfide binding may include DTT, DTE, 2-mercaptoethanol and so on, in the practice of the present invention there is no reason to limit to the use thereof. Representative surfactants capable of being used to modify the protein may include dodecyl sodium sulfate (SDS), Triton X $100^{(R)}$, Tween-$20^{(R)}$ and so on, but there is no reason to limit to the use thereof in the practice of the present invention. Yet, although typical chaotropic agents that can be used to modify the protein may includes GuSCN, NaSCN, GuClO4, NaclO4 and urea, there is no reason to limit to the use thereof in the practice of the present invention. The solid protein such as segments and so on can be modified with the use of a cutting agent or chemical serine-protease such as, for example, trypsin for digesting the protein. The protein may be of a native structure (not yet modified) for the purpose of Raman analysis or SERS analysis.

The metal complex quantum crystal of the present invention is precipitated on the metal to form the biochip and, therefore, it appears that the metal nanometric dots that function as metallic nanoparticles are apt to be ionized and, therefore, it is held in contact with the reagent (target molecule) within the aqueous solution. Accordingly, the biochip suitable for use in measurement of the surface enhanced Raman scatterings (SERS) can be suitably employed since it has a surface plasmon resonance enhancing effect, which is exhibited by the metal nanoparticles that are regularly arrayed, and an ionic metal property which forms the charge transfer complex together with target molecules (the inventors of the present invention call "it "submetallic property" because of the metallic property and the ion property both possessed by the biochip of the present invention.)

Metal complex to form a quantum crystal is selected to have a complex stability constant (log β) of the formula (I) to correlate the electrode potential E of the supported metal.

$$E°(RT/|Z|F)\ln(\beta_i) \qquad \text{Formula (I)}$$

Where E° is the standard electrode potential, R is the gas constant, T is absolute temperature, Z is the ion valence, F represents the Faraday constant.)

In case that the metal complexes can be selected from the group consisting of plasmon metals such as Au, Ag, Pt and Pd, the plasmon metals have a function of localized surface plasmon resonance enhancement effect for the Raman light.

In particular, when the metal complex is a silver complex, the complex may be formed by reaction of silver complexing agent having a stability constant (formation constant) (log $β_i$) of 8 or more with a silver halide, where a silver chloride may be preferably selected as the halide and the complexing agent may be preferably selected from the group consisting of thiosulfate salt, thiocyanate salt, sulfite salt, thiourea, potassium iodide, thiosalicylic acid salt, and thiocyanuric acid salt.

In case of the silver complex, the resulting quantum crystal has quantum dots made of nano-cluster having average diameter of 5~20 nm, so that the size of the quantum crystal will be in a range of 100 to 200 nm.

The concentration of the metal complex in the aqueous solution should be determined depending on the size of the quantum crystals mainly, and the concentration of a dispersing agent had better to be considered when using it, Typically, although the metal complex in the aqueous solution can be used in the range of 100 ppm to 5000 ppm, in order to prepare nano-sized particles called as the nano-cluster, it may be used preferably in a range of 500 to 2000 ppm depending on the functionality of the ligand of the metal complex The quantum crystals formed on a metal substrate or metal particles are believed to likely have a positive polarity in an aqueous solution as a metal complex crystals. Therefore, in order to adsorb the protein in a biological sample on a solid phase, so the solid phase should be subject to an alkali treatment in the presence of halide ions and to adjust the polarity, for example it can be carried out by dropping sodium hypochlorite solution of pH11 or more thereon. After the treatment, the quantum crystals is re-crystallized not only to have a negative polarity in an aqueous solution and also to form a meso-crystalline comprising silver oxide including silver peroxides, where proteins in a sample are possible to facilitate the immobilization on the bio-chip.

Proteins caused from the disease are contained in biological samples of urine, blood, plasma, serum, saliva, semen, slops, sputum, cerebral spinal fluids, tears, mucus, breath components and so on. The samples are diluted by aqueous or hydrophilic solvents to an appropriate concentration before dipping.

The total protein concentration in a biological sample can be measured and determined from the Raman spectrum obtained by irradiating a laser beam of a specific wavelength. FIG. 3 is a Raman spectrum wherein a serum sample of each colon cancer patients is diluted 10-fold, 100-fold, 500-fold, 1000-fold and 10000-fold with pure water and measured by 633 nm laser (30 mW), so as to obtain peak rising value (PSV) and peak integration value, which value tend to change with concentration. Therefore, it is understood that it is possible to perform a quantitative analysis of the total protein in the serum.

Therefore, it is possible to analyze the identification and progress of cancer from information such as the peak height, the peak integral values and the peak onset time of the resulting Raman spectrum. FIG. 1 shows a peak calculation method of Raman waveform, wherein from the spectrum of Raman scattering by 633 nm laser of human serum samples it is confirmed to form the peak of the scattering intensity in the vicinity of 1350 $cm^{-1}$ and 1550 $cm^{-1}$. Thus, on the basis of average value (m) between 800 $cm^{-1}$ (a) and 2000 $cm^{-1}$ (b) of scattering intensity the (p-m) peak rising value is defined as (Shifting Peak Value PSV) These peaks rise value and peak integral value are important in view of the cancer related substances in human serum, because it is possible to be an indicator of the identification and progression of cancer in conjunction with peak onset time.

BRIEF DESCRIPTION OF DRAWINGS

FIG. 1 shows a peak calculation method of the Raman wave, where spectra of the Raman scattering by 633 nm laser of human serum samples indicates the formation of a peak of scattering intensity in the vicinity of 1350 $cm^{-1}$ and 1550 $cm^{-1}$.

FIG. 8 is a graph showing a result of EDS spectra analysis of quantum crystals (elemental analysis).

DESCRIPTION OF EMBODIMENTS

Hereinafter, embodiments of the present invention will be explained, referring to the attached drawings,

Example 1

Figure 4:
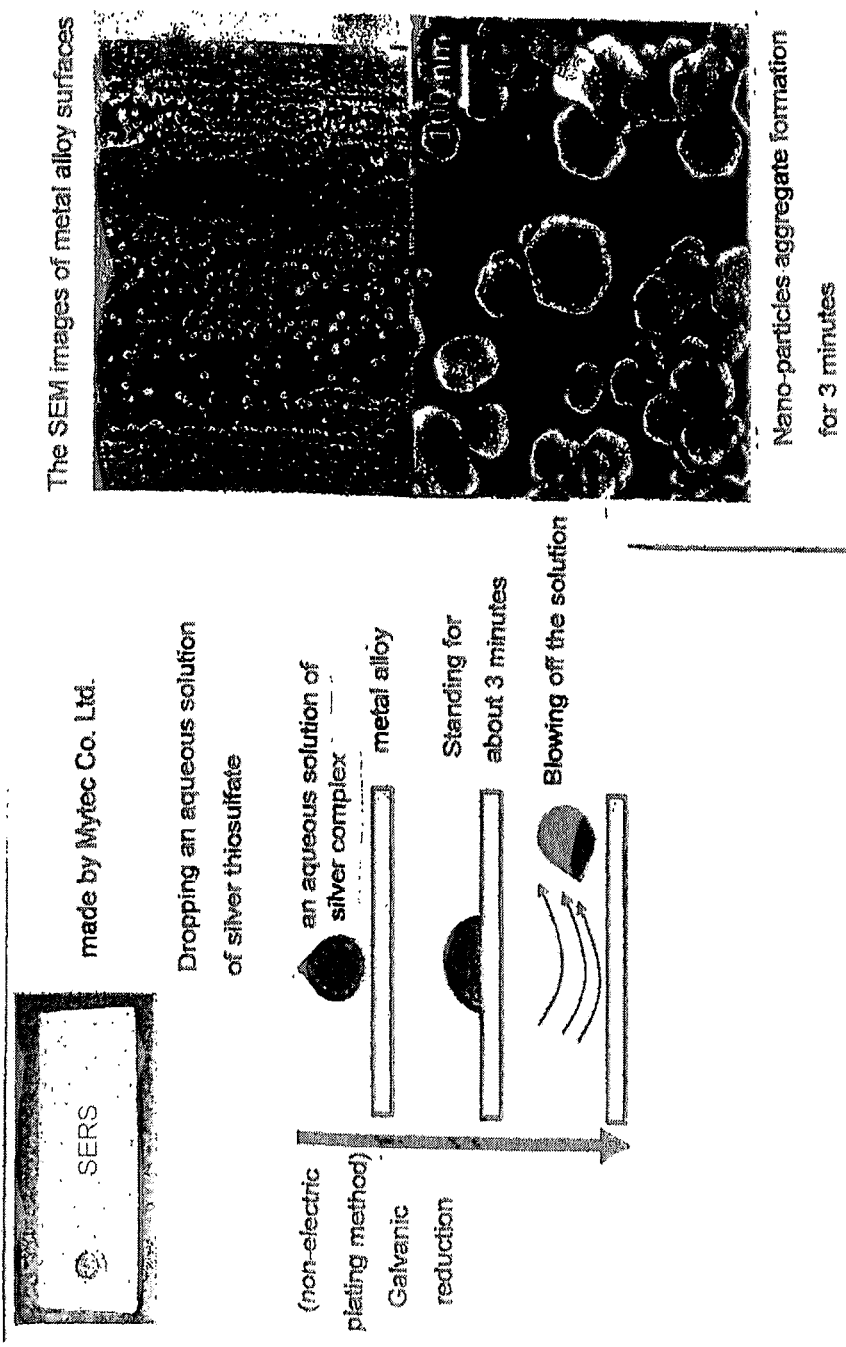
FIG. 4 is an explanatory diagram showing a making procedure of the present inventive new SERS substrate shown in Example 1, wherein an upper left photograph shows a substrate of Mytec Co. Ltd. with the SEM image.
Figure 5:
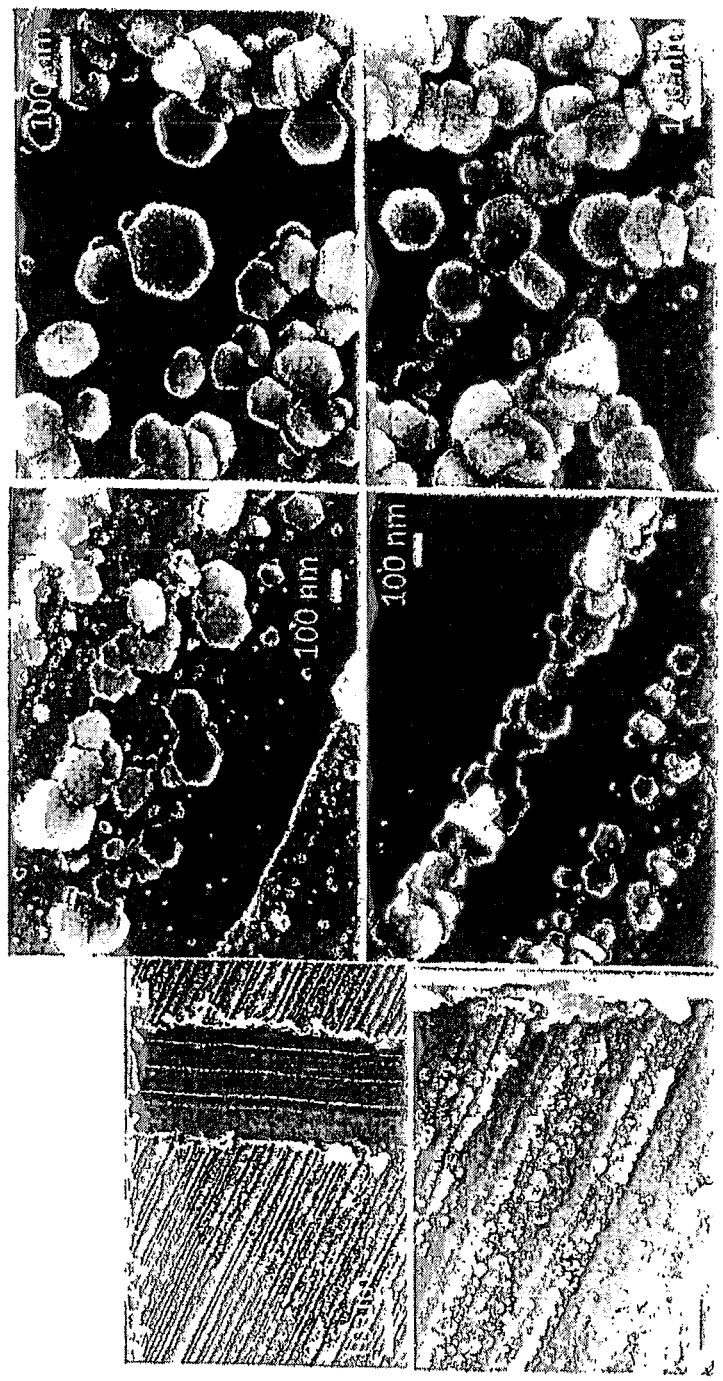
FIG. 5 is a photograph showing various SEM images of the nano-particle aggregate (quantum crystal) prepared in Example 1.
Figure 6:
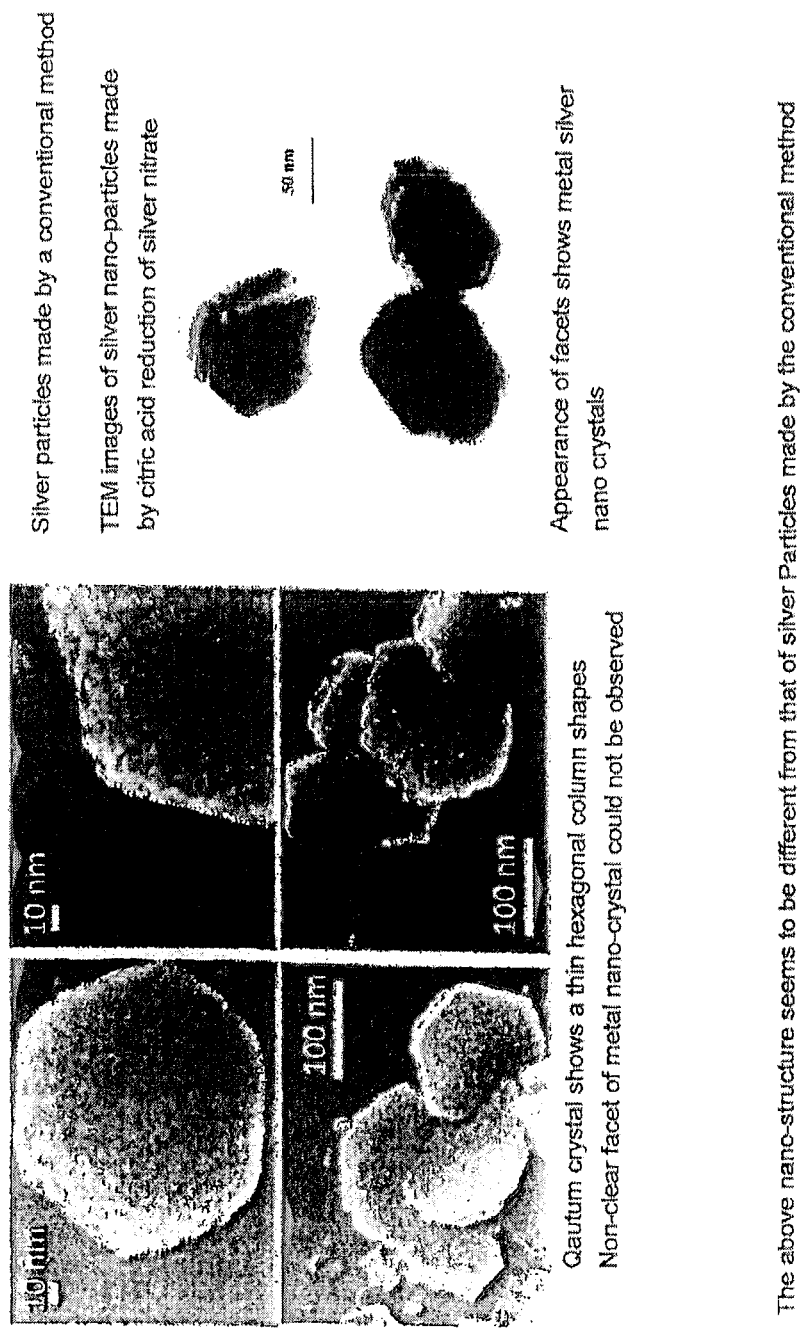
FIG. 6 is a photograph showing an enlarged SEM image of a nanoparticle.
Figure 7:
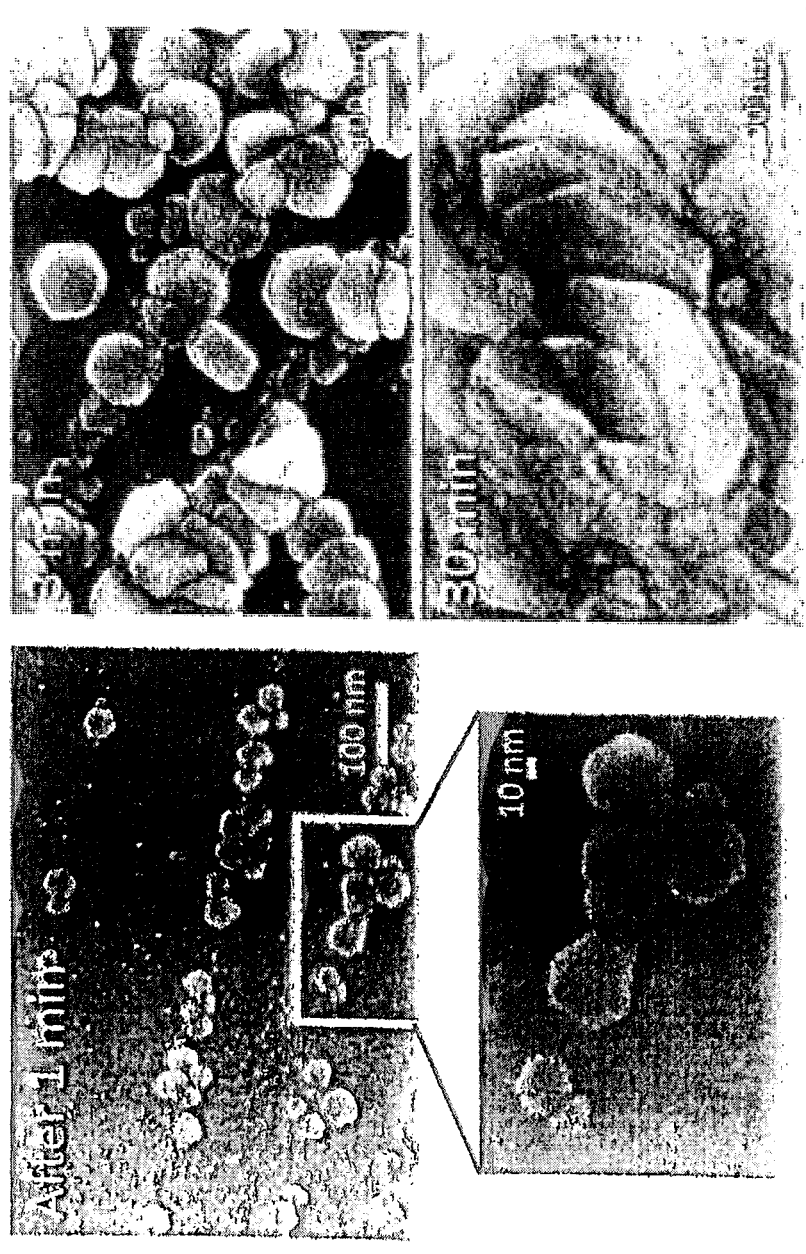
FIG. 7 is a photograph showing the relationship between quantum crystal shapes and standing times after dropping on the phosphor bronze substrate.
Figure 9:
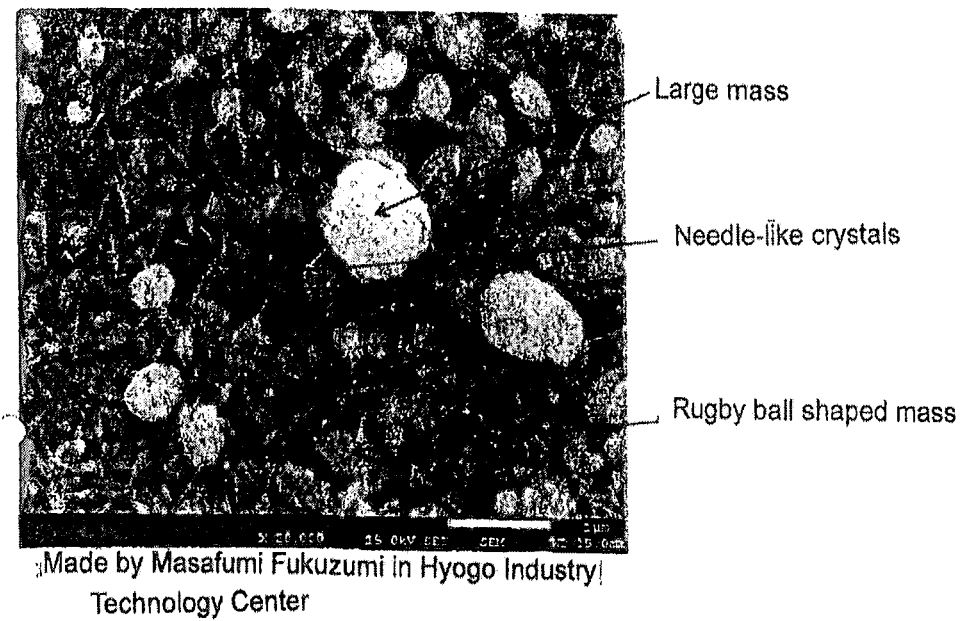
FIG. 9 is a photograph showing SEM image of quantum crystals alkali-treated in the presence of a halogen ion (Sodium hypochlorite treatment).
Figure 10A:
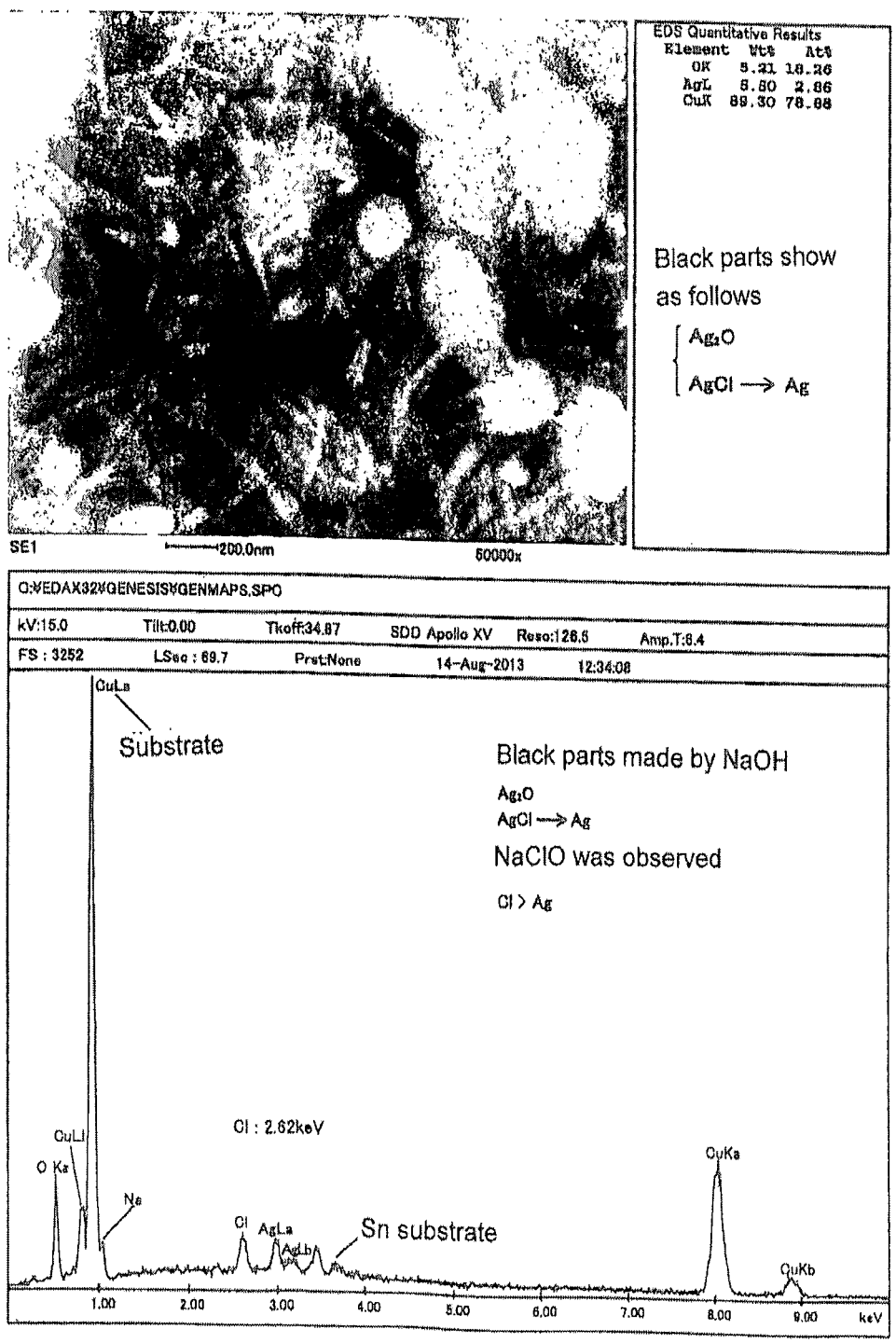
FIG. 10A is a photograph showing needle-like crystals of the alkali-treated quantum crystals.
Figure 10B:
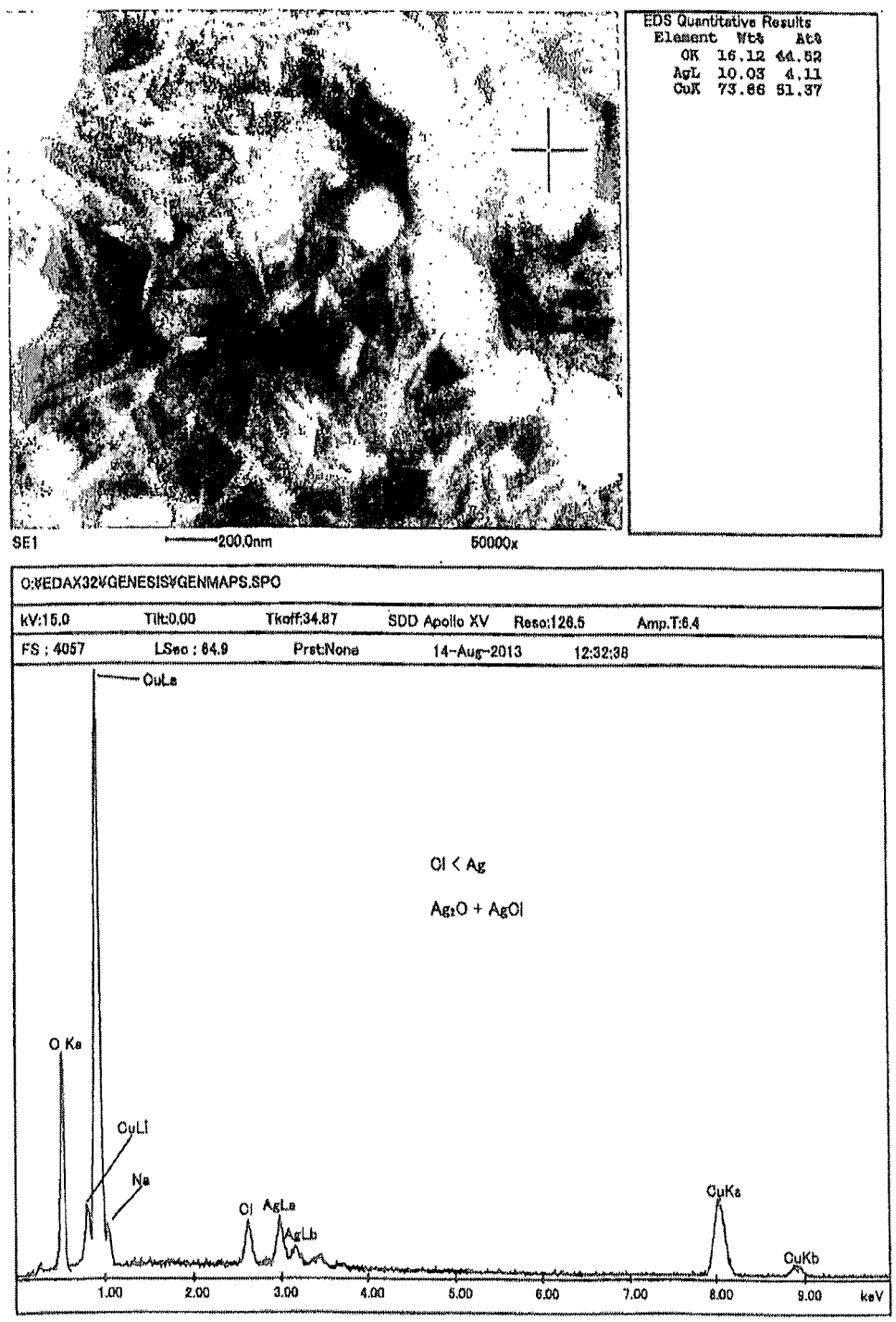
FIG. 10B is a photograph showing a rugby ball-shaped mass in the needle-like crystals.
Figure 10C:
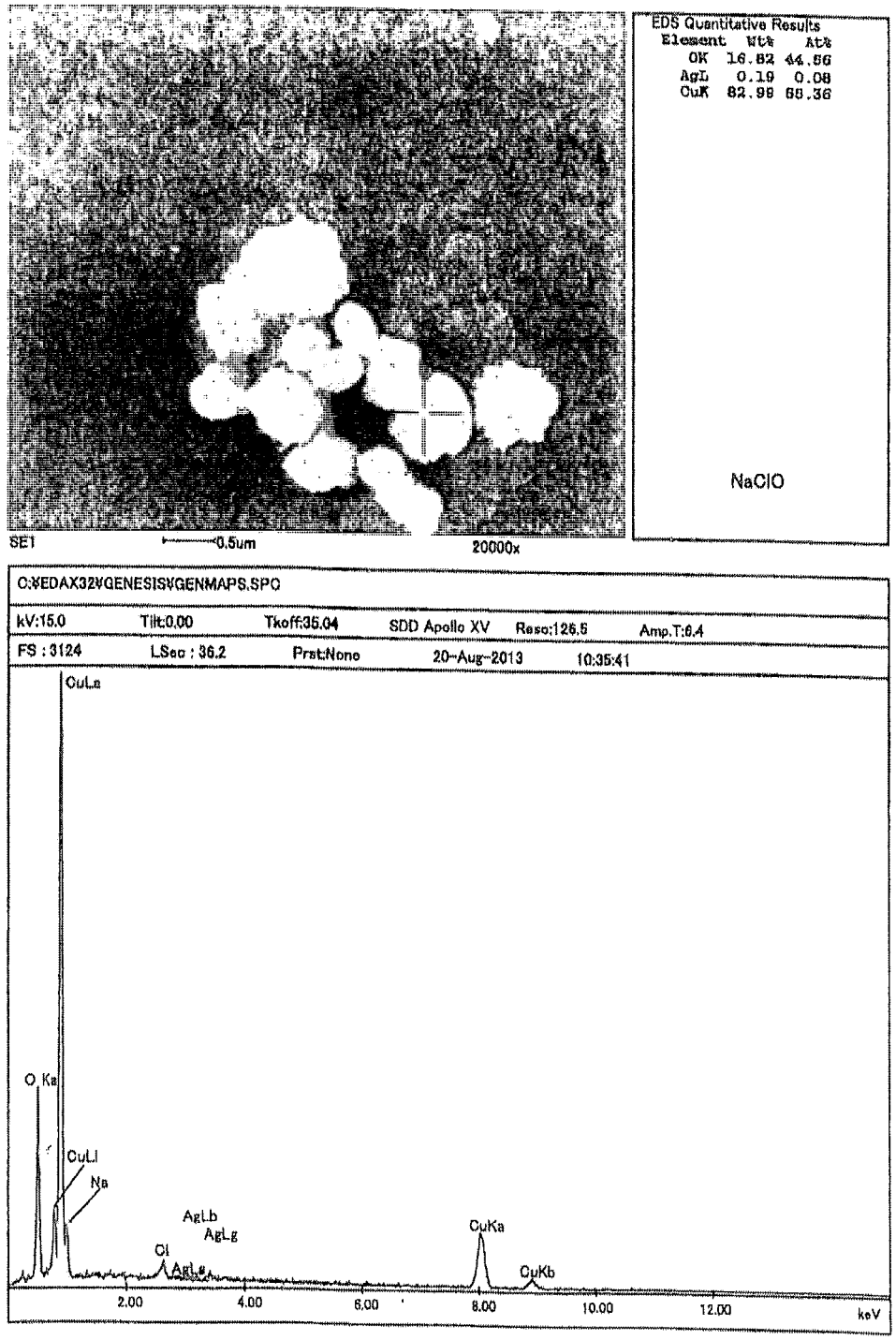
FIG. 10C is a graph showing a result of EDS spectra of large mass (elemental analysis).

As shown in FIG. 4, an aqueous solution containing 1000 ppm of silver thiosulfate was prepared and the 1 drop was added dropwise on a phosphor bronze plate. After standing for about 3 minutes, the solution on the plate was blown off. On the plate, quantum crystals were obtained as shown in the SEM image at the right side of FIG. 4. FIG. 5 is a photograph showing various SEM images of the nano-particle aggregate prepared in Example 1 (quantum crystal), and FIG. 6 shows an enlarged SEM image of nano-particles where there were thin hexagonal columnar crystals of 100 nm more or less and having an unevenness surface of several nm order. We could not find out any specific facets of metal nano-crystals in the quantum crystals. FIG. 7 is a photograph showing the relationship between quantum crystal shapes and the standing time after dropping onto the phosphor bronze substrate, where it is recognized that firstly, a hexagonal quantum crystal is produced and then growing while maintaining the crystal shape.

FIG. 8 is a graph showing a result of EDS spectra (elemental analysis). of the quantum crystals where not only silver but also elements derived from complex ligands can be detected in case of the quantum crystal on the phosphor bronze substrate, while only silver can be detected in the case of the quantum crystals formed on a copper plate by using 1000 ppm of silver thiosulfate in aqueous solution and keeping it for the standing time of 3 minutes after dropping onto the copper substrates.

(Discussion on Formation of the Quantum Crystal)

In case of 1000 ppm of silver thiosulfate complex in an aqueous solution, hexagonal column crystals of 100 nm more or less, are formed for the standing time of 3 minutes after dropping it onto a phosphor bronze plate, where it is confirmed that irregularities of several nm order are found on the hexagonal column quantum crystals from the SEM images (FIGS. 4, 5 and 6). and any specific facets derived from metal nano-crystals are not found, while the EDS elemental analysis shows silver and elements derived from the complexing ligand. Accordingly, it can be estimated from the above analysis, that the whole particles show nano-crystals of silver complex and also the unevenness appearance on the surface may be caused by the formation of spread quantum dots made of silver clusters in the complexes. From the aspect of phenomenon that the silver complex quantum crystals of the present invention can be formed on a phosphor bronze plate, while silver nanoparticles alone can be deposited on the copper substrate, it is estimated that, as the equilibrium potential of the silver thiosulfate complexes is 0.33 which is equivalent to the copper electrode potential with 0.34, there is deposited only silvers with 0.80 on the copper substrate. On the other hand, in case of a phosphor bronze plate with the electrode potential of 0.22, which is slightly less noble than that of the copper so that silver complex crystals seem able to be precipitated. The concentration of the silver complex in the aqueous solution should be in a dilute region of 500~2000 ppm, 2) the electrode potential of the metal substrate with respect to the equilibrium potential of the metal complex solution is slightly less noble, 3) the metal complex should be deposited by the electrode potential difference between the metal substrate and the metal complex. Further, in case of 1000 ppm of thiourea silver complex in aqueous solution, the same function can be observed.

Example 2

Figure 2A:
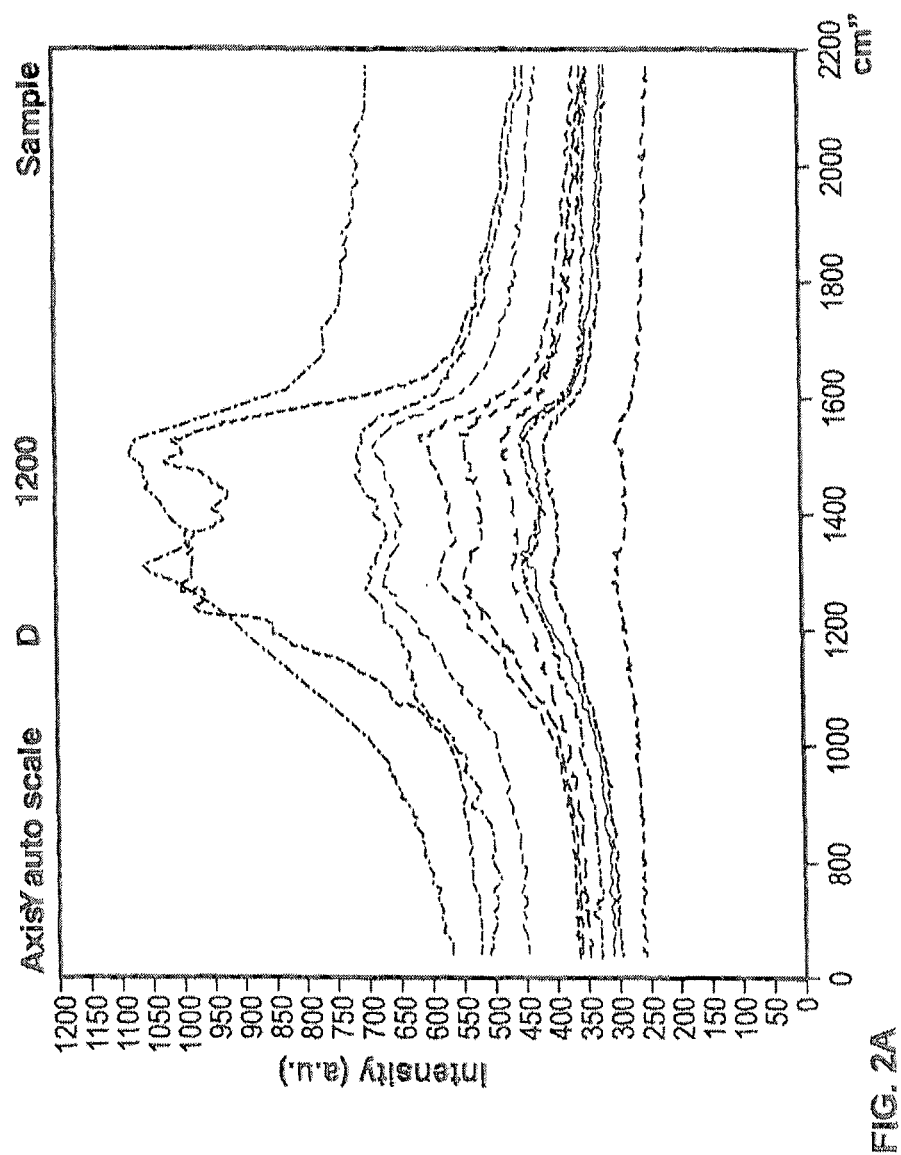
FIG. 2A is a Raman spectral diagram of a sample by adjusting the sera obtained from 12 cases of stomach cancer patients.
Figure 2B:
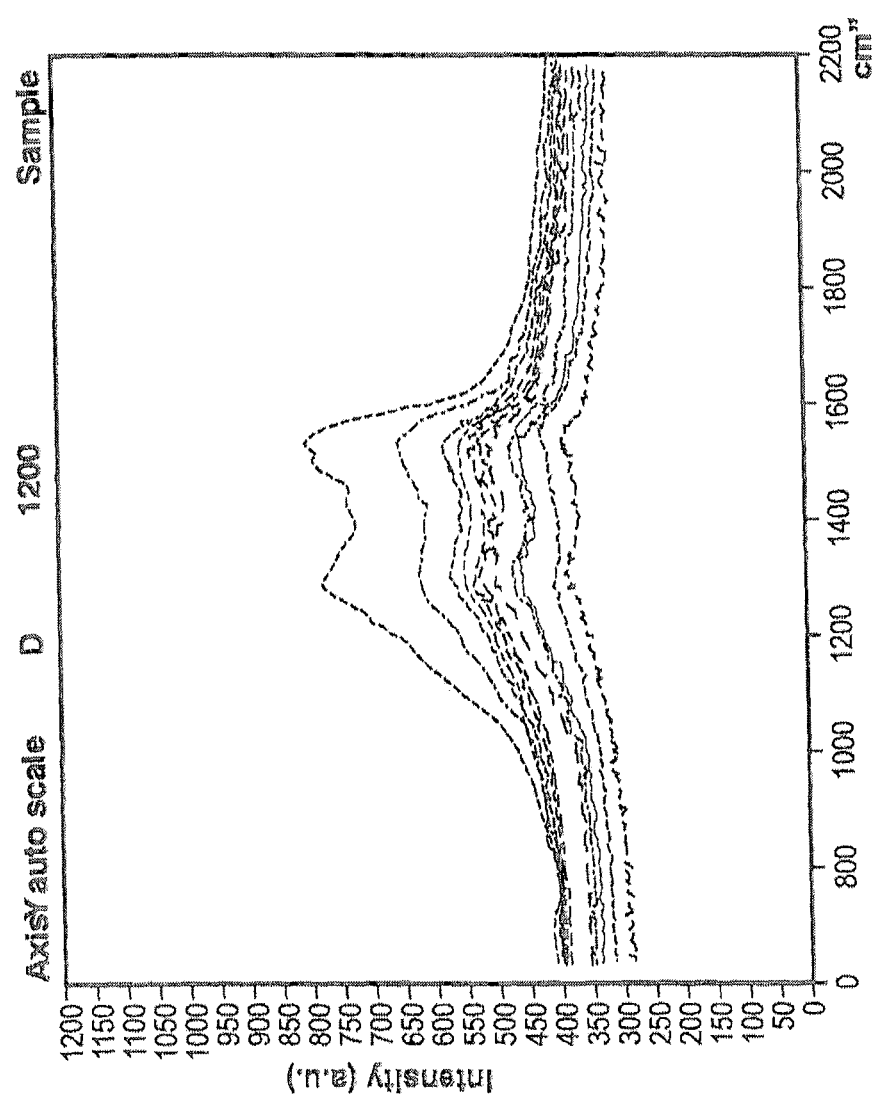
FIG. 2B is a Raman spectral diagram of a sample by adjusting the sera obtained from 12 cases of colorectal cancer patients.
Figure 2C:
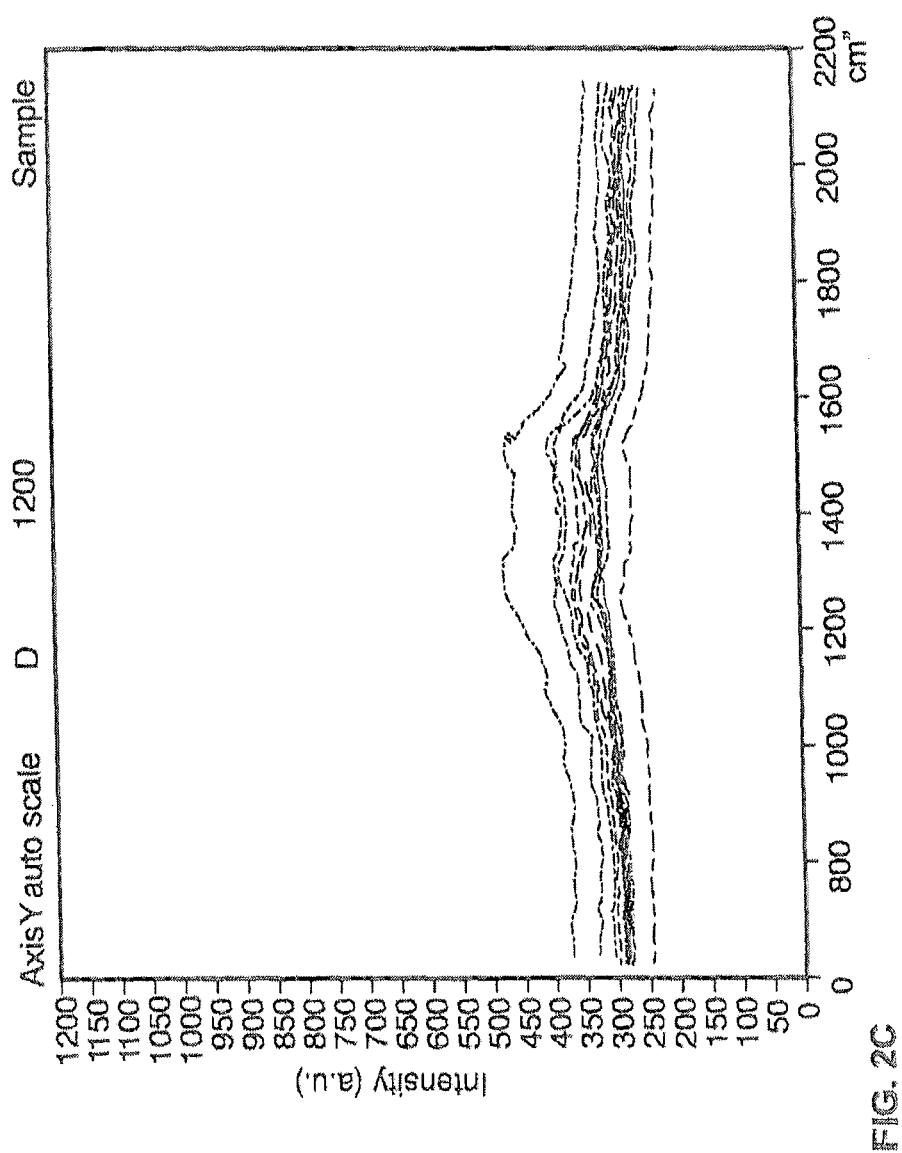
FIG. 2C is a Raman spectral diagram of a sample by adjusting the sera obtained from 12 cases of benign disease patients.
Figure 2D:
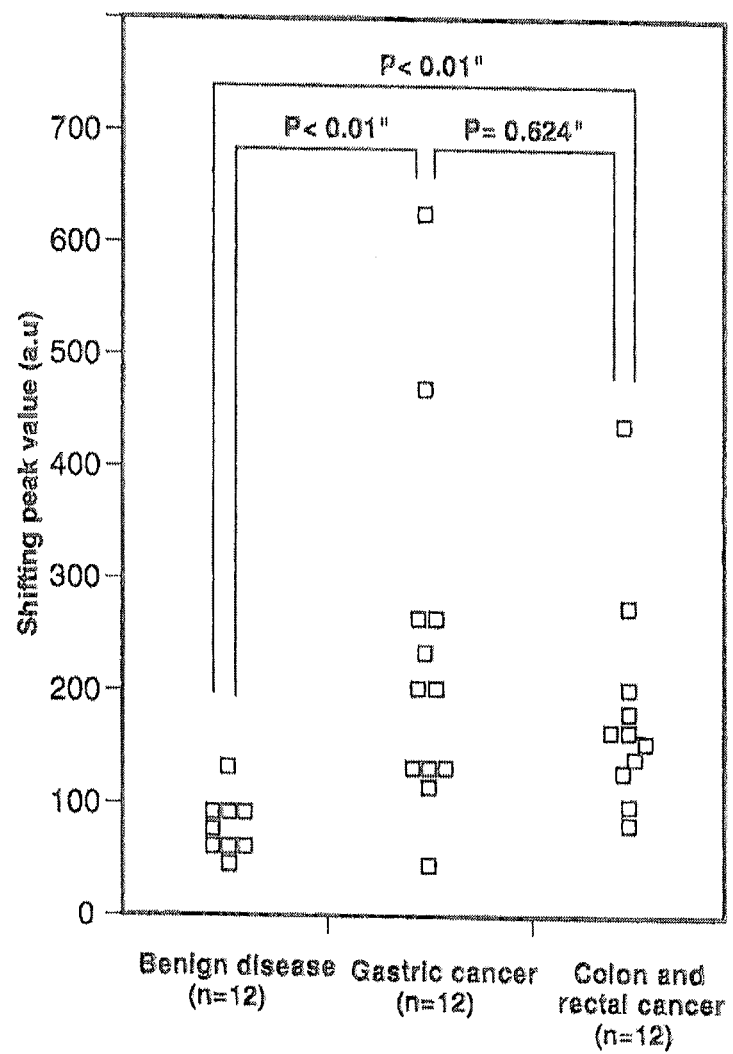
FIG. 2D is a graph showing a comparison of Raman scattering peak rising value of stomach cancer, colorectal cancer, and benign disease sample.
Figure 3:
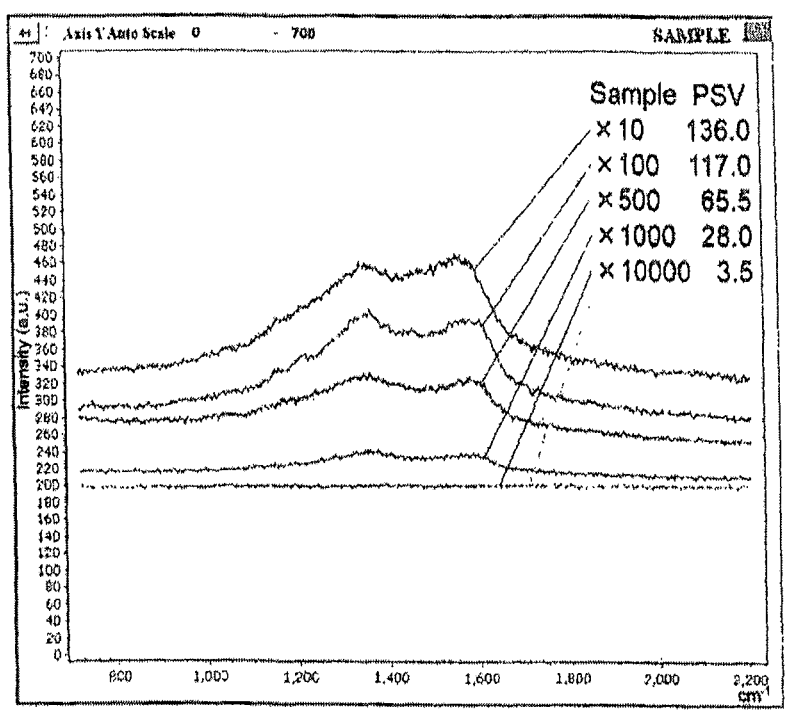
FIG. 3 is the Raman spectrum showing the relationship between diluted samples and the Raman scattering intensity where the diluted samples are obtained from 12 cases of colon cancer patients, which shows that the scattering intensity peak rising value and the sample concentration are correlative each other.
Figure 11:
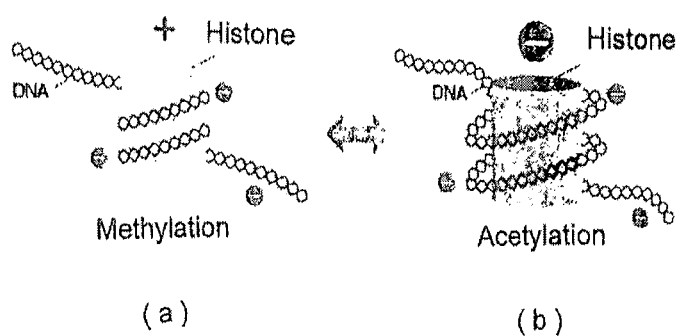
FIG. 11 is functional illustration views showing a state of the methylated free DNA (a) and a state of acetylated DNA (b).

On a substrate of silver thiosulfate quantum crystal made by using the phosphor bronze plate in Example 1, an aqueous solution of sodium hypochlorite having pH11 is dropped. After dropping of the aqueous solution, the solution is kept on the substrate and is brown off to prepare a bio-chip for SERS. On the other hand, the sera obtained from 12 cases of gastric cancer patients, the sera obtained from 12 cases of the colorectal carcinoma patients and the sera obtained from 12 cases of benign disease patients, all of them are diluted 10 times to prepare testing samples, which are subjected to a measurement of Raman spectra with irradiated with 633 nm laser light. There are observed much correlation between the degree of progress and the peak rise values as well as the peak integral value in case of gastric cancer and colon cancer. In addition, in the case of gastric cancer, the peak became to develop in the Raman spectrum after one minute of the laser irradiation, while in the case of colon cancer the peak became to develop in the Raman spectrum after 2-3 minutes after laser irradiation. Also, FIG. 2D is a graph showing a comparison of the Raman scattering peak rising values concerning gastric cancer, colon cancer and benign disease. The peak of the gastric cancer samples and colon cancer samples are found to be significantly higher than that of the benign disease samples. While it is difficult to find the difference between the gastric cancer sample and the colon cancer samples concerning the peak rise value, it can be recognized to show a possibility to identify both cancers by considering the peak expression times and the peak integral value. Here, the free DNA to be detected is a DNA wound around the protein called histones, which wound unit structure (1 set) is called a nucleosome and the structure which comes to a string shape of nucleosome gathered is called a chromatin (fibers). And, when the cells were into a cancerous state and divided repeatedly, DNA becomes to wrap around the histone not so as to come out the genes (tumor suppressor gene) inconvenient to increase the cancer and the DNA winding onto the histone becomes more tightly by methylation not so as to make the DNA loosen from the histones easily. Usually the histones are charged as (+), while the DNA is charged as (−), so that the two are stuck like a magnet and the methylation makes the two not to loosen easily where the methylated DNA wound around the histones is charged to the (+) state (see FIG. 11(*a*)). On the other hand, acetylation makes histone changed into charge (−), so that DNA of (−) becomes to act repulsively to the histones changed into the (−) state by the acetylation, resulting in expression of genes due to the unwound mechanism of the 'thread' of DNA from the histones (see FIG. 11(*b*)). Therefore, in order to selectively adsorb or trap the free DNA derived from cancer cells as the DNA wound around the histones, the substrate to absorb or trap the cancer related substances (+) in the sample is considered to have preferably a state of charge (−) in the sample for analysis.

(Discussion on the Meso-Crystal of Silver Oxide Compound: Part 1)

Figure 12:
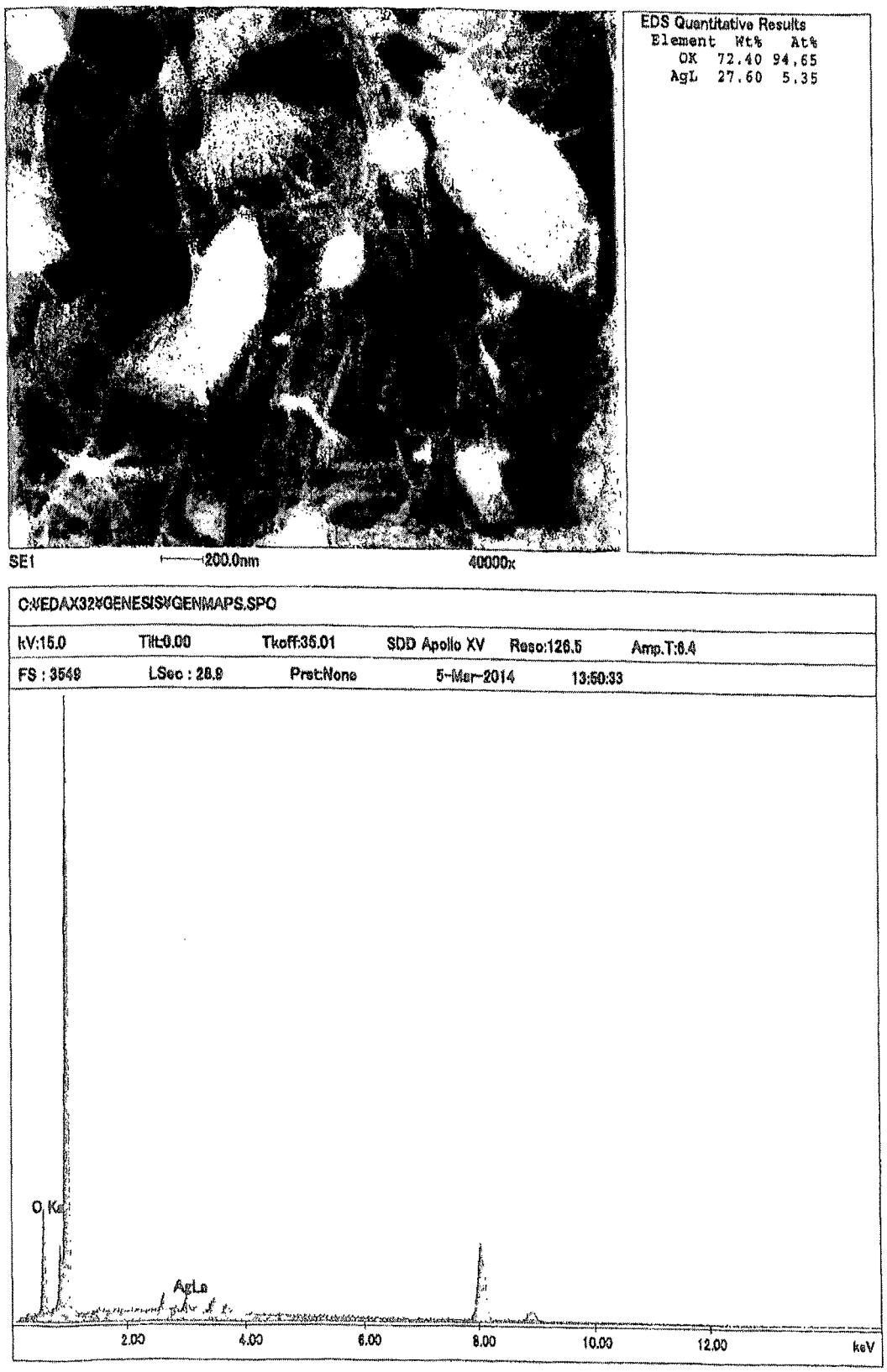
FIG. 12 is a view (top) of SEM image showing a re-crystallized substrate which is the quantum crystal substrate alkali treated in the presence of a halogen ion (Sodium hypochlorite treatment) (top view) and a graph (below) showing a result (elemental analysis) of the EDS spectra of the re-crystallized substrate.

The quantum crystal substrate is subjected to a treatment of dropping 5% sodium hypochlorite solution thereon and the dropped solution is removed off 2 minutes later to obtain crystals having structures shown in FIG. 12, where needle-shaped crystals and large clumps such as rugby ball-like mass are observed, so that the respective compositions are subjected to analyzation at EDS spectra (elemental analysis). After a result of the analysis, the needle-like crystals are both considered to consist of a composite crystal of silver oxide and silver chloride, from the following reaction formulas and the result of FIG. 12 does not show any chlorine and shows that the silver and oxygen is dominant.

$$Na_2S_2O_3 + 4NaClO + H_2O \rightarrow Na_2SO_4 + H_2SO_4 + 4NaCl \quad (1)$$

$$Ag^+ + NaCl \rightarrow AgCl + Na^+ \quad (2)$$

$$Ag^+ + 3NaOCl \rightarrow 2AgCl + NaClO_3 + 2Na^+ \quad (3)$$

$$Ag^+ + OH^- \rightarrow AgOH \quad (4)$$

$$2Ag^+ + 2OH^- \rightarrow Ag_2O + H_2O \quad (5)$$

Thus, although it is considered that silver ions and thiosulfate ions are important in the formation of meso-crystal according to the present invention by alkaline oxidation reaction in the presence of chloride ions and, although the silver oxide is formed according to a conventional reaction, it is surprisingly estimated that silver peroxide are predominantly formed from the following XPS measurement.

(Discussion of the Meso-Crystal of Silver Oxide Compound: Part 2)

Figure 13:
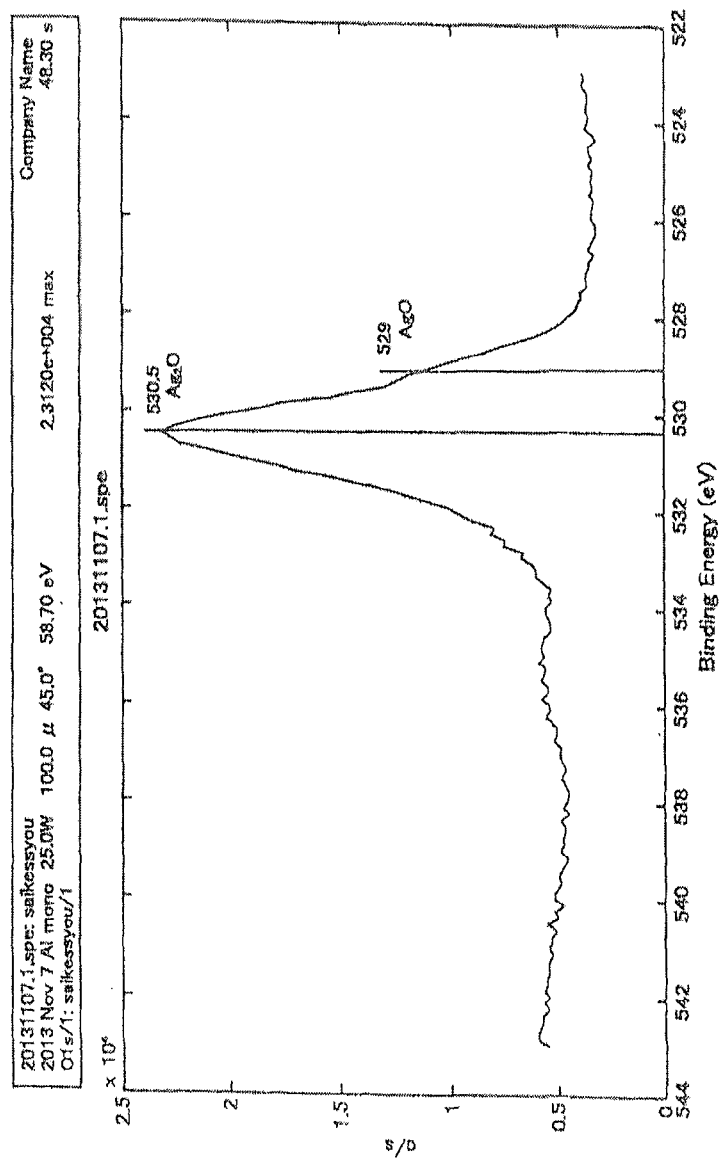
FIG. 13 is a graph showing a result of XPS measurement of the alkali-treated recrystallization substrate.
Figure 14:
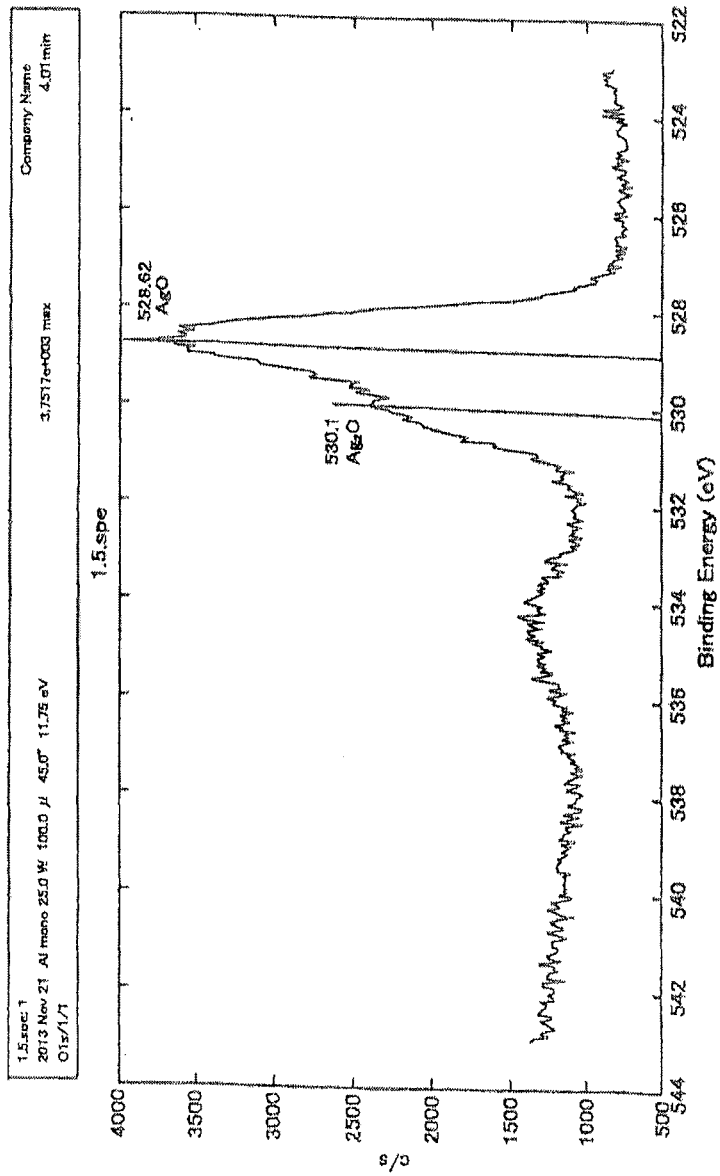
FIG. 14 is a graph showing a result of XPS measurements after etching the surface of the recrystallization substrate.

XPS Measurement:

The aqueous sodium hypochlorite was added dropwise to the quantum crystal substrate prepared as the above for 2 minutes, to make a re-crystal substrate, which is subjected to a XPS analysis (using models: ULVAC-PHI (Ltd.)/PHI5000 Versa Probe II (scanning X-ray photoelectron spectroscopy) for Ag and O by XPS measurement without etching. In addition, for comparison, Ag in the powder of silver chloride and the powder of silver oxide were measured. On the other hand, the recrystallized substrate was subjected to XPS measurement of Ag and O after etching for 5 minutes with an argon gas cluster ion gun. If the XPS measurement results of FIGS. 13 and 14 will be combined with the results of EDS according to FIG. 12, the peak in the vicinity of 529 eV is the peak derived from silver peroxide (AgO), while the peak in the vicinity of 530 eV is the peak derived from silver oxide ($Ag_2O$). Further, If it is etched, the oxygen content decreases, while the 0 peak derived from the silver peroxide (AgO) in the vicinity of 529 eV is still greater than the peak derived from the silver oxide in the vicinity of 530 eV in case of etching, so that it is recognized that the silver peroxide was produced in the vicinity of the substrate. It is assumed that the electrode potential of the substrate and the catalytic action are affected. to the meso-crystal formation The EDS measurement was carried on the above-mentioned re-crystal substrate by using a JEOL Ltd./JSM-7001F (field emission scanning electron microscope analysis). In addition, even if the aqueous solution selected from the group consisting of hypochlorous acid, 0.01 N sodium hydroxide, 0.01 N hydrochloric acid and 0.1 molar sodium carbonate would be used, any result similar to be treated with sodium hypochlorite was not obtained, Thus, it is believed that the formation of the needle-like crystals are caused by the above reaction in the presence of silver ions and thiosulfate ions. While the silver oxide is induced into negatively charged in an aqueous solution, it is reduced by the light to deposit metallic silver. Further, since silver peroxide shows more remarkable in the above tendency than silver oxide, it is possible to adsorb cancer related substances having a positive charge, resulting in occurrence of the surface plasmon enhancement effect between the trapped cancer related substance and the silver particles.

INDUSTRIAL APPLICABILITY

Thus, according to the present invention, by using the other biological sample selected from the group consisting of urea, blood, blood plasma, blood serum, saliva, seminal fluid, human waste, cerebral fluid, tear, mucin, exhaled component and so on, it is possible not only to detect protein profiles specific to the particular diseases and provide an early stage diagnosis and information of the disease progress by simple method, but also to selectively trap each of disease related substances, the judgement of each of diseases can be made by the measurement of Raman spectra.

The invention claimed is:

1. A method of preparing a meso-crystal product comprising shaped meso-crystal of silver oxides comprising a silver oxide and a silver peroxide on a plasmon metal selected from the group consisting of Au, Ag, Pt and Pd, the method comprising:
providing a carrier comprising a metal or alloy having an electrode potential less noble than that of the plasmon metal;
providing a metal complex aqueous solution having a metal complex content of 500 to 2000 ppm;
adding the metal complex aqueous solution on the carrier to form a quantum crystal of the metal complex; and
re-crystallizing the quantum crystal into a meso-crystal comprising metal oxides by an alkali treatment in a presence of halogen ion, wherein the meso-crystal has a negative charge after the meso-crystal is recrystallized, wherein the metal complex has a complex stability constant (log β) and the carrier has an electrode potential E that is less than an electrode potential E° as shown in the following equation:

$$E° = (RT/|Z|F)\ln(\beta) \quad (1)$$

wherein E° is a potential of the metal complex in an aqueous solution, R is a gas constant, T is an absolute temperature, Z is an ion valence, and F represents a Faraday constant.

2. The method of claim 1, wherein the meso-crystal product comprises a meso-crystal of silver oxides comprising a silver oxide and a silver peroxide on a metal carrier comprising a Cu or Cu alloy and having a less noble electrode potential than that of Ag, wherein the meso-crystal product not only shows surface enhanced resonance phenomenon by irradiation of an exciting light thereon but also shows a negative charge in water.

3. The method of claim 2, wherein the meso-crystal has a negative charge after the meso-crystal is recrystallized from a quantum crystal of silver thiosulfate by an aqueous solution of sodium hypochlorite.

4. The method of claim 1, wherein the metal complex comprises a silver complex, and the silver complex is obtained by a reaction of a silver halide and a complexing agent having a complex stability constant (log β) of 8 or more, the complexing agent being selected from the group consisting of thiosulfate, thiocyanate, sulfite, thiourea, potassium iodide, thiosalicylic acid salt, thiocyanuric acid salt and combinations thereof.

5. The method of claim 1, wherein the metal complex comprises silver thiosulfate, the carrier comprises a Cu or Cu alloy, the quantum crystal is made on the carrier from the silver thiosulfate, and re-crystallization of the silver thiosulfate is carried out using an aqueous solution of sodium hypochlorite by an alkali treatment in the presence of chloride ion.

6. A method of preparing a meso-crystal product comprising a silver oxide nanocrystal comprising predominantly silver (I), (III) oxide, the method comprising:

providing a metal carrier comprising Cu or Cu alloy having an electrode potential less noble than that of silver;

providing a silver complex aqueous solution having a silver complex content of 500 to 2000 ppm;

adding the silver complex aqueous solution on the carrier to form a quantum crystal of the silver complex; and re-crystallizing the quantum crystal of the silver complex into a meso-crystal comprising silver oxide nanocrystal comprising predominantly silver (I), (III) oxide by an alkali treatment in a presence of a halogen ion and polarity adjustment, wherein the silver complex has a complex stability constant (log β) and the carrier has an electrode potential E that is less than an electrode potential E° as shown in the following equation $$E° = (RT/ZF)\ln(\beta) \quad (1)$$

wherein E° is a potential of the silver complex in an aqueous solution, R is a gas constant, T is an absolute temperature, Z is an ion valence, and F represents a Faraday constant.

7. The method of claim 6, wherein the metal complex comprises a silver complex, and the silver complex is obtained by a reaction of a silver halide and a complexing agent having a complex stability constant (log β) of 8 or more, the complexing agent being selected from the group consisting of thiosulfate, thiocyanate, sulfite, thiourea, potassium iodide, thiosalicylic acid salt, thiocyanuric acid salt and combinations thereof.

8. The method of claim 6, wherein the metal complex comprises silver thiosulfate, the carrier comprises a Cu or Cu alloy, the quantum crystal is made on the carrier from the silver thiosulfate, and re-crystallization of the silver thiosulfate is carried out using an aqueous solution of sodium hypochlorite by an alkali treatment in the presence of chloride ion.

9. The method of claim 6, wherein the meso-crystal product comprises a silver oxide nano-crystal comprising predominantly silver (I), (III) oxide on a metal carrier comprising Cu or Cu alloy and having a less noble electrode potential than that of silver.

10. The method of claim 6, wherein the meso-crystal has a negative charge after the meso-crystal is recrystallized from a quantum crystal of silver thiosulfate by an aqueous solution of sodium hypochlorite.

* * * * *